United States Patent
Lingwood

(12) 
(10) Patent No.: US 6,218,147 B1
(45) Date of Patent: Apr. 17, 2001

(54) HAEMOPHILUS ADHESIN PROTEIN

(75) Inventor: Clifford A. Lingwood, Toronto (CA)

(73) Assignee: HSC Research & Development Limited Partnership, Toronto (CA)

( * ) Notice: Subject to any disclaimer, the term of this patent is extended or adjusted under 35 U.S.C. 154(b) by 0 days.

(21) Appl. No.: 09/456,287

(22) Filed: Dec. 8, 1999

Related U.S. Application Data

(62) Division of application No. 08/686,528, filed on Jul. 26, 1996, now Pat. No. 6,054,134.

(51) Int. Cl.$^7$ ................................................. C12N 15/09
(52) U.S. Cl. ........................ 435/69.3; 435/69.1; 435/71.1; 435/243; 435/252.3; 536/23.1; 536/23.7; 424/256.1
(58) Field of Search .................... 536/23.1, 24.1, 536/23.7, 24.3, 24.32, 24.33; 435/320.1, 69.1, 69.3, 71.1, 243, 252.3; 530/350; 424/256.1, 257.1

(56) References Cited

U.S. PATENT DOCUMENTS

| | | | |
|---|---|---|---|
| 5,646,259 | 7/1997 | St. Geme, III et al. | 536/23.1 |
| 5,656,436 | 8/1997 | Loosmore et al. | 435/67.1 |
| 5,679,547 | 10/1997 | Krivan et al. | 435/69.3 |

OTHER PUBLICATIONS

Tatusov et al. Curr. Biol. Mar. 1996. 6(3): 279–291.*
Dimmock, N.J., (1982), J. Gen. Virol., 59:1–22.
McClintock, P.R., (1988), New York: Springer–Verlag, 97–101.
Sharon et al, (1981), Ciba Found. Symp., 80:119–141.
Lingwood, C.A., (1993), CRC Press, Boca Raton, FL, 209–222.
Lingwood et al, (1987), J. Biol Chem, 262:8834–8839.
Lingwood et al, (1991), Biochem. Biophys. Res. Comm., 173:1076–1081.
Lingwood et al, (1992), Infect Immun., 60:2470–2474.
Jagannatha H. et al, (1991), Microb. Pathogen., 11:259–268.
Krivan et al., (1991), Biochem Biophys Res Commun., 175:1082–1089.
Yu et al, (1994), Infect Immun., 62:5213–5219.
Gupta et al, (1994), Infect Immun., 62:4572–4579.
Lee et al, (1994) Mol Microbiol., 11:705–713.
Zhang et al, (1994), Infect Immun., 62:4367–4373.
Brennan et al, (1991), J Biol Chem., 266:18827–18831.
Lockhoff et al, (1991), Chem. Int. Ed. Engl., 30:1611.
Kyte et al, (1982), J. Molec. Biol., 157:112–122.
Lingwood et al, (1989), Lancet ii, 238–241.
Krivan et al, (1988), Arch. Biochem. Biophys., 260:493–496.
Gold et al, (1993), Infect Immun, 61:2632–2638.
Lingwood et al, (1993), Infect Immun., 61:2474–2478.
Fleischmann et al, (1995), Rd. Science, 269:496–512.
Stromberg N et al, (1988), FEBB lett. 232:193–198.
Krivan H. et al, (1989), J Biol Chem., 264:9283–9288.
Raza M.W. et al, (1993), Epidimiol. Infect., 11039–347.
Dytoc M. et al., (1993), Infect. Immun., 61:448–456.
Ji et al., (1995), Proc. Nat'l. Acad. Sci., 92(26):12055–9.
Rey et al., (1993), Mol. Microbiol., 8:471–81 (1993).

* cited by examiner

Primary Examiner—Jennifer Graser
(74) Attorney, Agent, or Firm—Burns, Doane, Swecker & Mathis, LLP

(57) ABSTRACT

An adhesin protein which binds specifically to phosphatidylethanolamine (PE), gangliotriaosylceramide ($Gg_3$) and gangliotetraosylceramide ($Gg_4$) has been isolated and purified from *H. influenzae*. Also provided are immunogenic compositions and methods of protecting susceptible mammals from diseases caused by bacterial pathogens having the adhesin as a surface protein.

9 Claims, 11 Drawing Sheets

HAEMOPHILUS ADHESIN PROTEIN

This application is a divisional of application Ser. No. 08/686,528, filed Jul. 26, 1996, now U.S. Pat. No. 6,054,134.

FIELD OF THE INVENTION

The present invention relates to the isolation of lipid-binding adhesins and, more specifically, to the isolation and identification of a lipid-binding adhesin from *Haemophilus influenzae*.

BACKGROUND OF THE INVENTION

Various journal articles referred to herein are identified by number in parentheses and are listed, with full citations, at the end of the specification.

*Haemophilus influenzae* is a respiratory pathogen which colonises human, mucosal surfaces and is associated with otitis media, sinusitis, conjunctivitis, bronchitis, pneumonia, meningitis, epiglottitis and cellulitis [1, 2]. The natural habitat and reservoir for this organism is the upper respiratory mucosal surfaces, primarily the nasopharynx [3]. Mucosal surfaces are ports of entry and major sites of many infectious agents. Many pathogens, including viruses [4, 5], bacteria [6, 7] and bacterial toxins [8] bind to specific carbohydrate moieties on the mucosal surfaces, enabling colonization and infection and potentially mediating a toxic effect on the host cells. These carbohydrate moieties may be present in either glycolipids or glycoproteins. For example, many respiratory pathogens recognise gangliotriaosylceramide (GalNAc$\beta$1-4gal$\beta$1-4glc cer [$Gg_3$]), gangliotetraosylceramide (gal$\beta$1-3galNAc$\beta$1-4gal$\beta$1-4glc cer [$Gg_4$]) [7, 9–15] and sulfatoxygalactosylceramide [SGC] [16, 17]. Respiratory pathogens have also been identified which recognize phosphatidylethanolamine (PE). PE, $Gg_3$ and $Gg_4$ are also recognised by such pathogens as *Pseudomonas aeruginosa*, Burholderia cepacia Chlamydia trachomatis, C. pneumoniae, Neisseria meningitis, enteropathogenic *Escherichia coli*, and *H. pylori* (9–14, 26, 29, 32).

There is a need for new means of combatting infections due to these pathogens, as antibiotic resistance becomes increasingly common. A vaccine to stimulate the production of antibodies which would interfere with the attachment of these pathogens to their target cells would be of great assistance in combatting such infections.

SUMMARY OF THE INVENTION

The present invention provides a purified and isolated adhesin protein of about 46 kDa from strains of *Haemophilus influenzae*. The adhesin binds specifically to phosphatidylethanolamine (PE), gangliotriaosylceramide ($Gg_3$) and gangliotetrasylceramide ($Gg_4$). This adhesin protein is referred to herein as "adhesin".

The invention also provides purified and isolated nucleic acid molecules encoding an adhesin protein of a strain of *H. influenzae* or a fragment or analogue of the adhesin.

The adhesin protein, fragments or analogues thereof, nucleic acid molecules encoding the adhesin or encoding fragments or analogues thereof and vectors containing such nucleic acid molecules are useful in immunogenic compositions for immunising against diseases caused by pathogens which bind to their target cells by means of an adhesin which binds to phosphatidylethanolamine (PE), gangliotriaosylceramide ($Gg_3$) and gangliotetraosylceramide ($Gg_4$).

The nucleic acid molecules provided herein are also useful for amplifying a specific DNA target sequence using PCR, and as probes to locate specific, unique DNA sequences.

The nucleic acid molecules provided herein are also useful for production of the encoded adhesin protein or fragments or analogs thereof, free of other Haemophilus proteins, by expression of the nucleic acids in a recombinant DNA expression system.

The invention also provides antibodies raised against the purified adhesin of the invention. These antibodies are useful for the treatment of patients infected by *H. influenzae* and other pathogens which also bind to phosphatidylethanolamine (PE), gangliotriaosylceramide ($Gg_3$) and gangliotetrasylceramide ($Gg_4$).

In accordance with one embodiment of the present invention, there is provided a substantially pure adhesin protein which binds specifically to phosphatidylethanolamine (PE), gangliotriaosylceramide ($Gg_3$) and gangliotetraosylceramide ($Gg_4$).

In accordance with a further aspect of the invention an adhesin protein is provided comprising the amino acid sequence MKKLLKISAISAALLSAPMMANADVLAS-VKPLGFIVSSIADGVTGTQVLVPA GASPHDYN-LKLSDIQKVKSADLVVWIGEDIDSFLDK-PISQIERKKVITIADL ADVKPLLSKAHHEHFHEDGDHDHDHKHE-HKHDHKHDHDHDHDHKHEHKHDHE HHDHDH-HEGLTTNWHVWYSPAISKIVAQKVADKL-TAQFPDKKALIAQNLSDF NRTLAEQSEKITAQLANVKDKGFYVFH-DAYGYFNDAYGLKQTGYFTINPLVA PGAKTLA-HIKEEIDEHKVNCLFAEPQFTP-KVIESLAKNTKVNVGQLDPIGDK VTLGKNSYATFLQSTADSYMECLAK.

In accordance with another aspect of the invention, a recombinant adhesin protein or fragment or analogue thereof is provided produced by expression of the nucleotide sequence in an appropriate vector.

In accordance with another aspect of the invention is an immunogenic composition comprising at least one active component selected from the group consisting of:

(a) a purified and isolated nucleic acid molecule encoding an adhesin protein which binds specifically to PE, $Gg_3$ and $Gg_4$ or a fragment or analogue of said protein;

(b) a purified and isolated nucleic acid molecule having the nucleotide sequence of Table 1 or a nucleotide sequence complementary thereto;

(c) an adhesin protein which binds specifically to PE, $Gg_3$ and $Gg_4$ or an effective analogue or fragment thereof; and (d) a recombinant adhesin protein and a pharmaceutically acceptable carrier, said at least one active component producing an immune response when administered to a mammal.

In accordance with another aspect of the invention is an immunogenic composition formulated as a vaccine for administration to a mammal to protect the mammal against diseases caused by bacterial pathogens having the adhesin protein as a surface protein.

In accordance with another aspect of the present invention, a method is provided of protecting a susceptible mammal against a disease caused by a bacterial pathogen having as a surface protein, an adhesin protein which binds specifically to phosphatidylethanolamine (PE), gangliotriaosylceramide ($Gg_3$) and gangliotetraosylceramide ($Gg_4$), the method comprising administering to the mammal an effective amount of an immunogenic composition. The immunogenic composition comprises at least one active component selected from the group consisting of:

(a) a purified and isolated nucleic acid molecule encoding an adhesin protein which binds specifically to PE, $Gg_3$ and $Gg_4$ or a fragment or analogue of said protein;

(b) a purified and isolated nucleic acid molecule having the nucleotide sequence of Table 1 or a nucleotide sequence complementary thereto;

(c) an adhesin protein which binds specifically to PE, $Gg_3$ and $Gg_4$ or an effective analogue or fragment thereof; and (d) a recombinant adhesin protein and a pharmaceutically acceptable carrier, said at least one active component producing an immune response when administered to a mammal.

According to another aspect of the invention is an antibody or antiserum specific for an isolated and purified adhesin protein, a recombinant adhesin protein or an immunogenic composition containing adhesin protein.

According to another aspect of the invention is a method for producing a substantially pure adhesin protein which bind specifically to PE, $Gg_3$, $Gg_4$ comprising the steps of:

(a) providing a bacterial strain which produces said adhesin protein;

(b) growing said bacterial strain to provide a cell mass;

(c) harvesting the cell mass by centrifugation;

(d) extracting the cell mass to provide an adhesin-containing extract;

(e) applying the adhesin-containing extract to a PE affinity matrix;

(f) eluting unbound proteins from the matrix; and (g) releasing the adhesin protein from the matrix to provide a substantially pure adhesin protein.

In accordance with another aspect of the invention, an isolated nucleic acid molecule is provided encoding an adhesin protein which binds specifically to phosphatidylethanolamine (PE), gangliotriaosylceramide ($Gg_3$) and gangliotetraosylceramide ($Gg_4$).

BRIEF DESCRIPTION OF THE DRAWINGS

The invention, as exemplified by preferred embodiments, is described with reference to the accompanying drawings in which.

Figure 1:
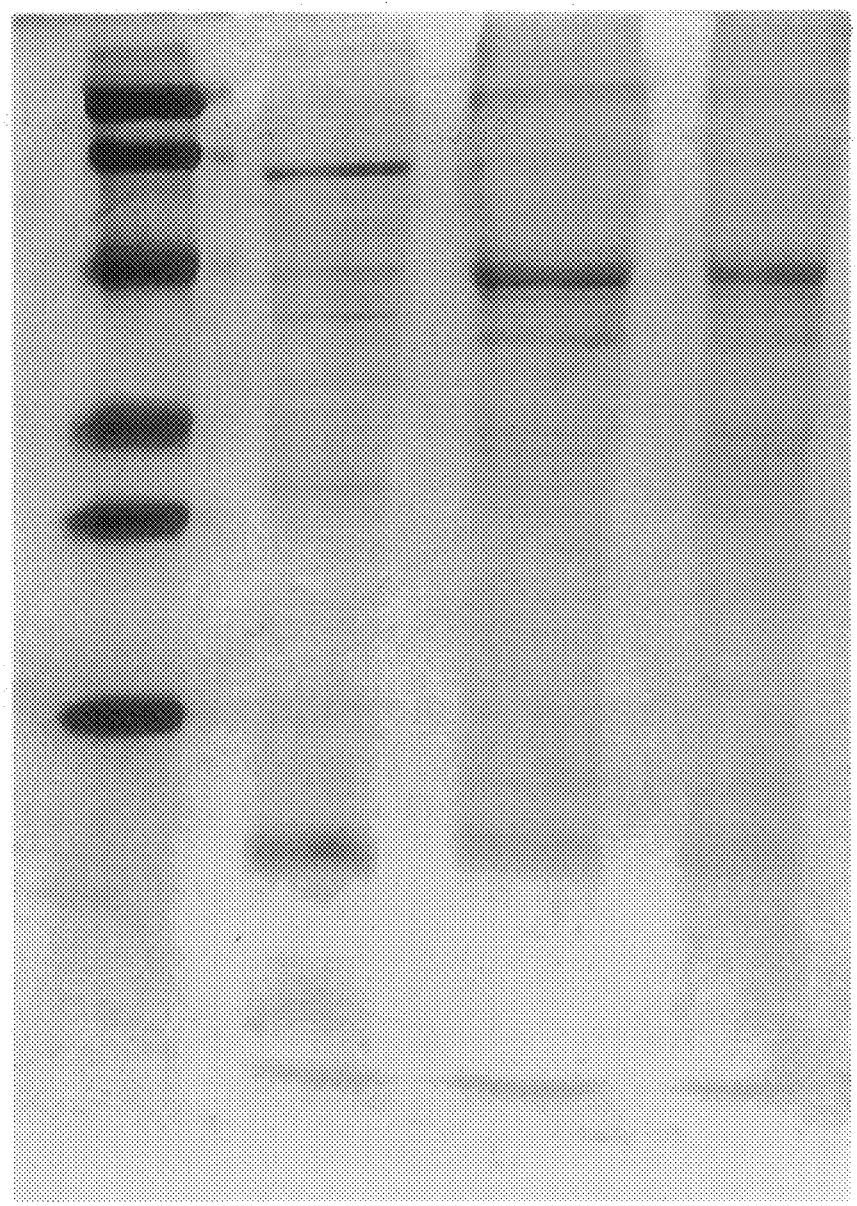
FIG. 1 shows SDS-PAGE gel of adhesin preparations, stained with silver, as follows.

Lane A: molecular weight markers: phosphorylase B (106 kDa), bovine serum albumin (80 kDa), ovalbumin (49.5 kDa), carbonic anhydrase (32.5 kDa), soybean trypsin inhibitor (27.5 kDa), lysozyme (18.5 kDa);

Lane B: Water extract of *H. influenzae* type b(10 μg protein);

Lane C: PE chromatography/EDTA elution purified adhesion protein from *H. influenzae* type b (1 μg protein);

Lane D: PE chromatography/EDTA elution purified adhesin protein from *H. influenzae* nontypeable strain (260 ng).

FIG. 2, Panel A, shows inhibition of binding (expressed as cpm $^{125}$I) of *H. influenzae* organisms, type b (■) or untypeable (□), to PE by water extracted proteins (X axis: μg protein added).

FIG. 2, Panel B, show inhibition of binding (expressed as cpm $^{125}$I) of *H. influenzae* organisms, type b (closed symbols) or untypeable (open symbols), to PE (▲,△) or $Gg_3$ (■,□) by purified adhesin from untypeable *H. influenzae* (X axis: μg protein/ml.

Figure 3A:
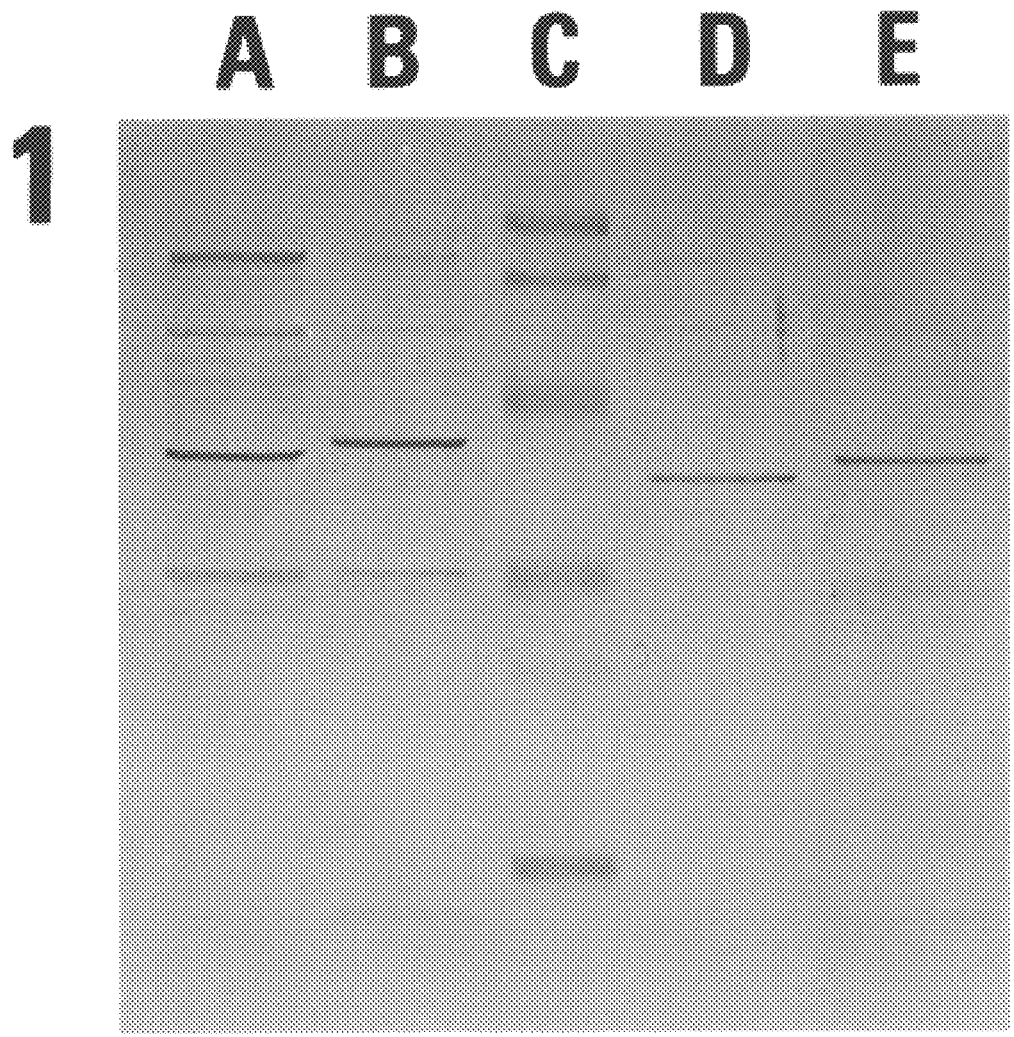
Figure 3B:
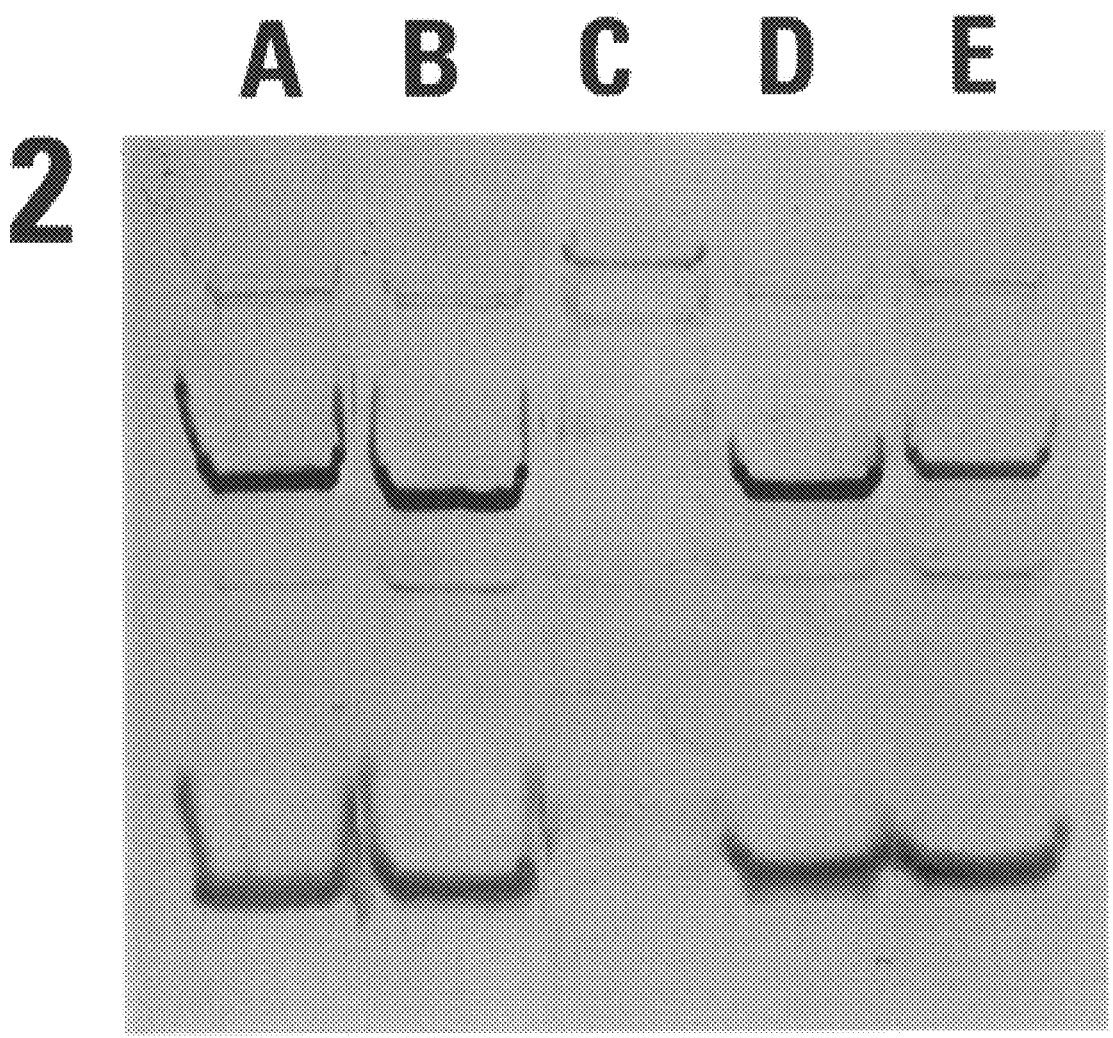

FIGS. 3A and 3B show Western blots of water extracts (Panel 1) or SDS extracts (Panel 2) of four clinical *H. influenzae* isolates, Lanes A, B, D and E. Molecular weight markers in Lane C are as in FIG. 1.

Figure 4:
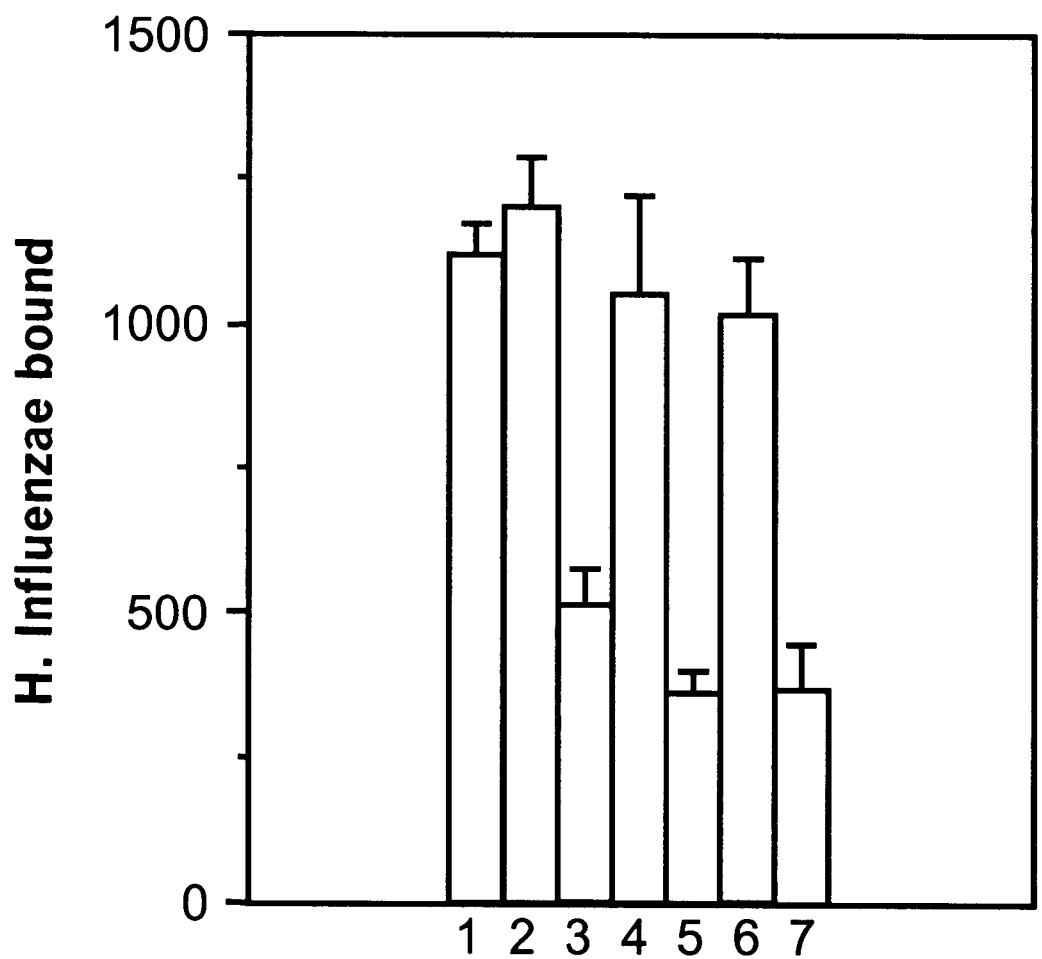

FIG. 4 shows control *H. influenzae* binding to HEp-2 cells, bar 1; binding following preincubation with 2%, 5% or 10% nonimmune serum: bars 2, 4, 6; or with 2%, 5% or 10% anti-adhesin: lanes 3, 5, 7. Inhibition was highly significant and p values were calculated at 0.003, 0.0022 and 0.0004 for 2%, 5% and 10% non-immune serum respectively.

Figure 5:
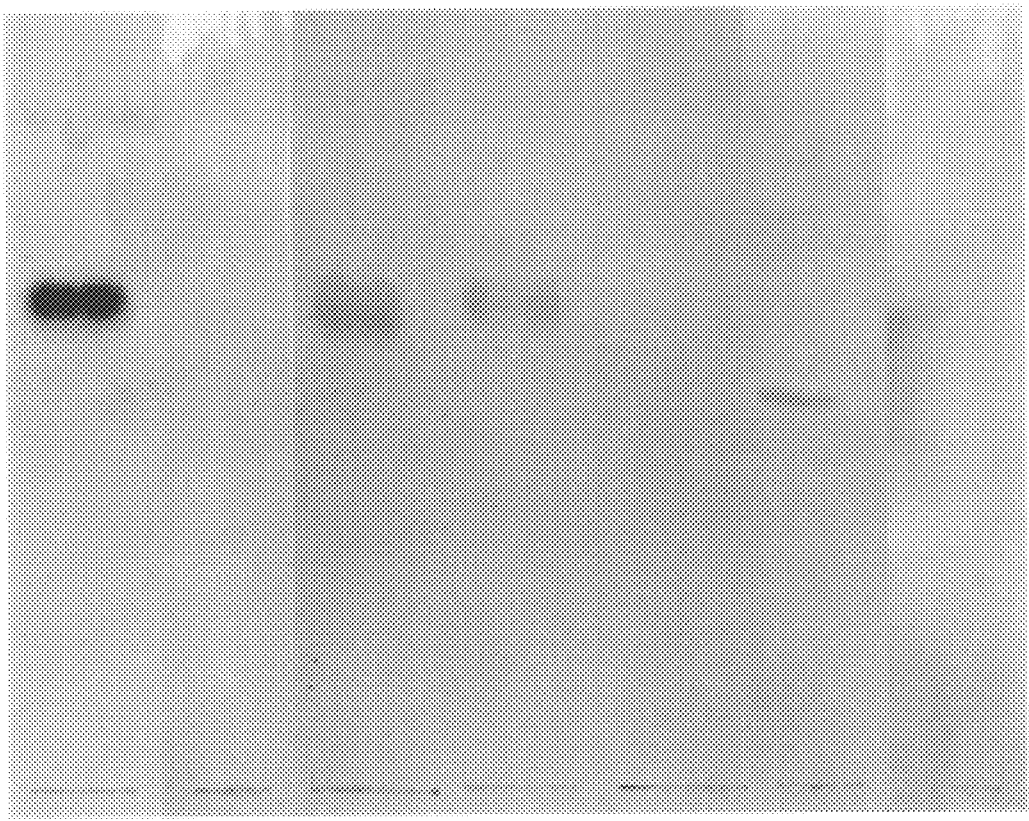

FIG. 5 shows tlc overlay results of binding of *H. influenzae* to soybean PE (lanes A to E) or to $Gg_3$ (lanes F and G) in the presence of 1% anti-adhesin immune serum (lanes B, E and G), non-immune serum (lanes A, D and F), or anti-*H. influenzae* (whole organism) serum (lane C). Lanes A and B; C, D and E; and F and G represent experiments with three different *H. influenzae* cultures respectively.

Figure 6:
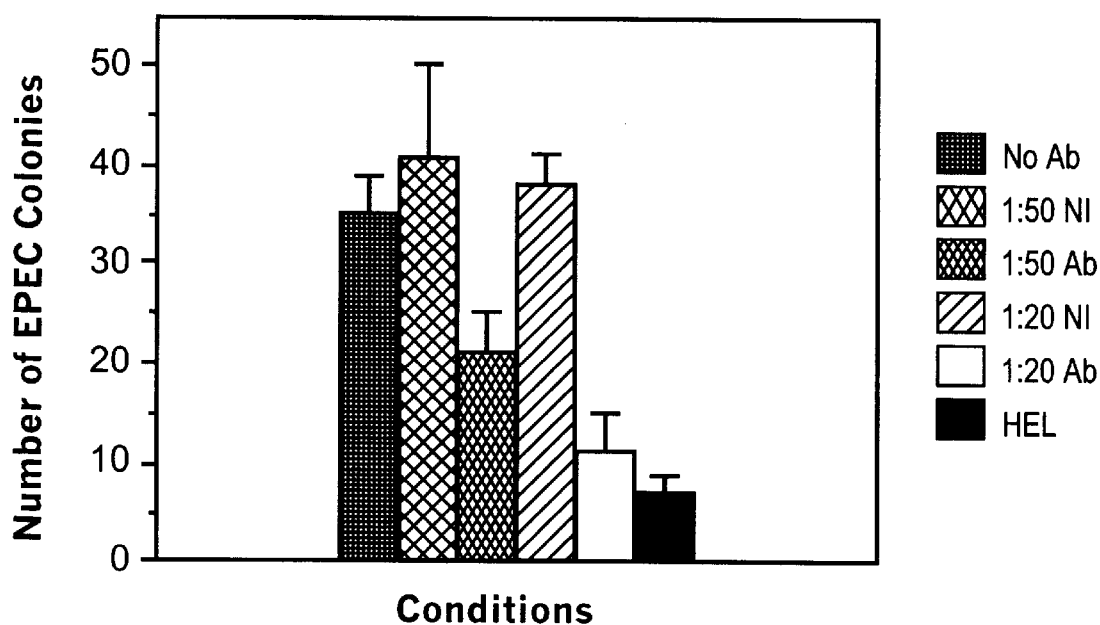

FIG. 6 shows inhibition of EPEC binding to HEp-2 cells by anti-*H. influenzae* adhesin antibody. (NI=non-immune serum, HEL=human embryonic lung fibroblasts).

Figure 7A:
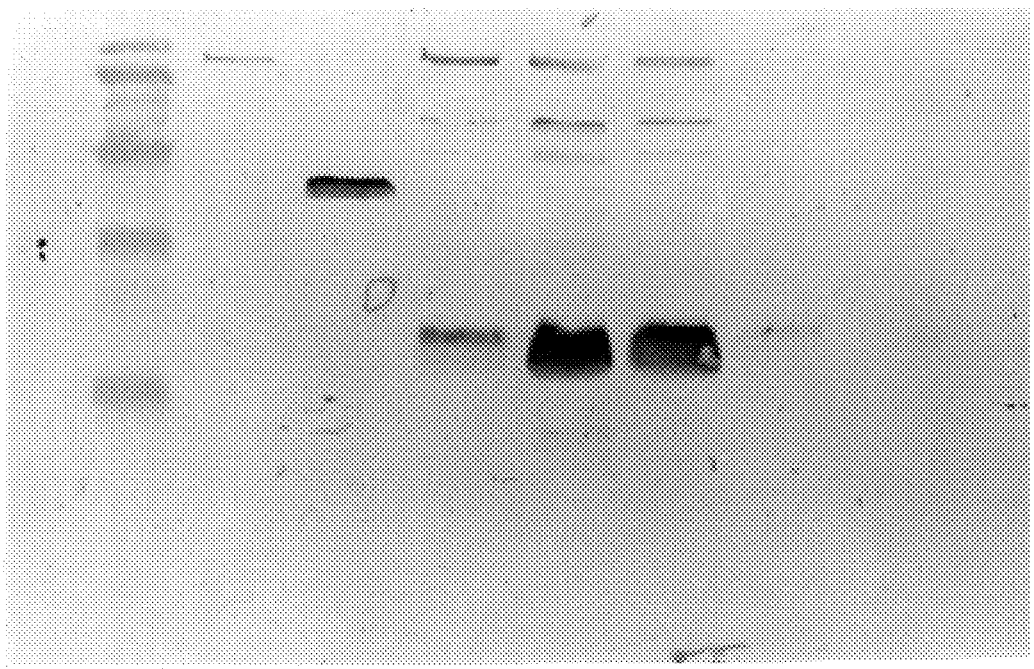

FIGS. 7A to 7D show cross-reactivity of anti-adhesin antibodies with EPEC and *H. pylori*. FIG. 7A, Lane 1 shows the water extract of HB101, a non-pathogenic lab *E. coli* strain. Lane 2 shows reactivity with the GST-adhesin recombinant protein of haemophilus. Lane 3 and lane 4 show the reactivity of water extract of the EPEC strain E2348. Lane 5 shows the water extract from E2348 which was unbound on a PE column. Lane 6 shows the material that was bound and eluted from a PE column.

Figure 7B:
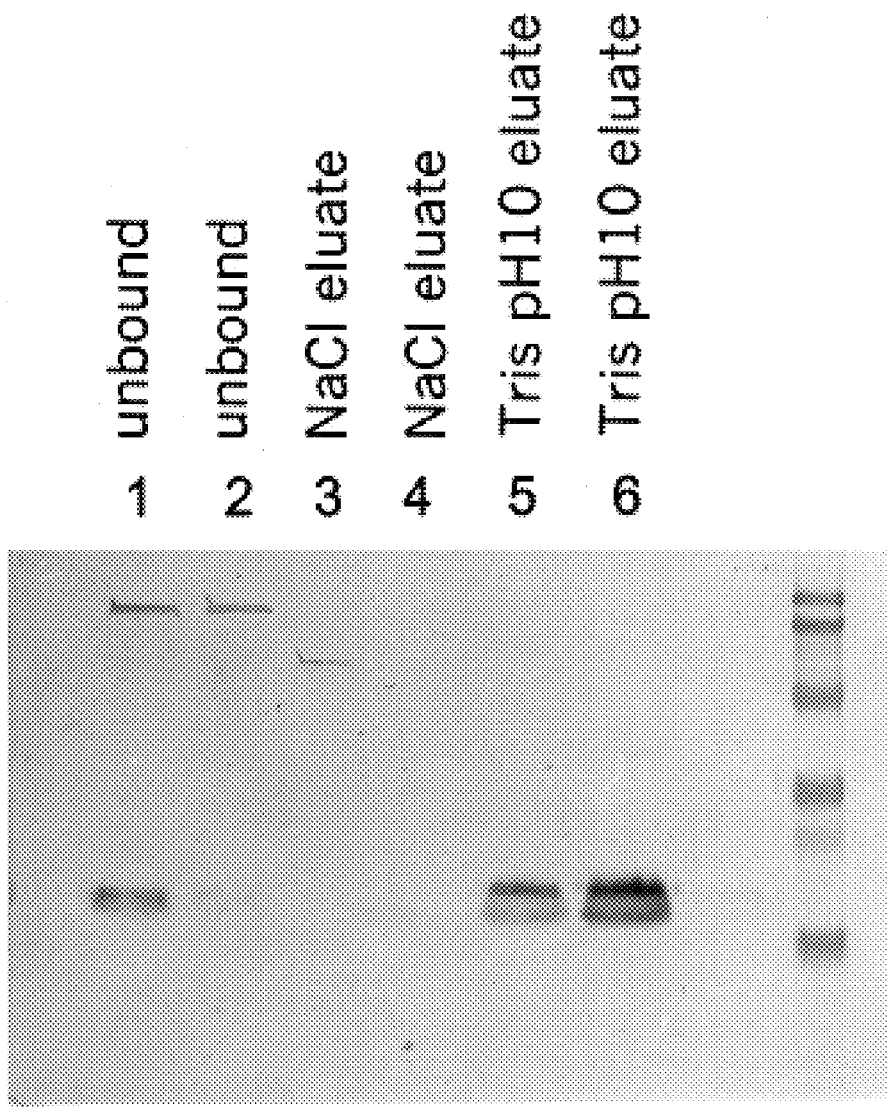

FIG. 7B shows the results of PE-affinity purification of the cross-reactive protein from EPEC. Lanes 1 and 2 show the unbound fraction. Lanes 3 and 4 show the sodium chloride eluted material from the PE column. Lanes 5 and 6 shown the Tris pH10 eluate from the PE column. The cross-reactive 20 kDa band is eluted under high pH conditions.

Figure 7C:
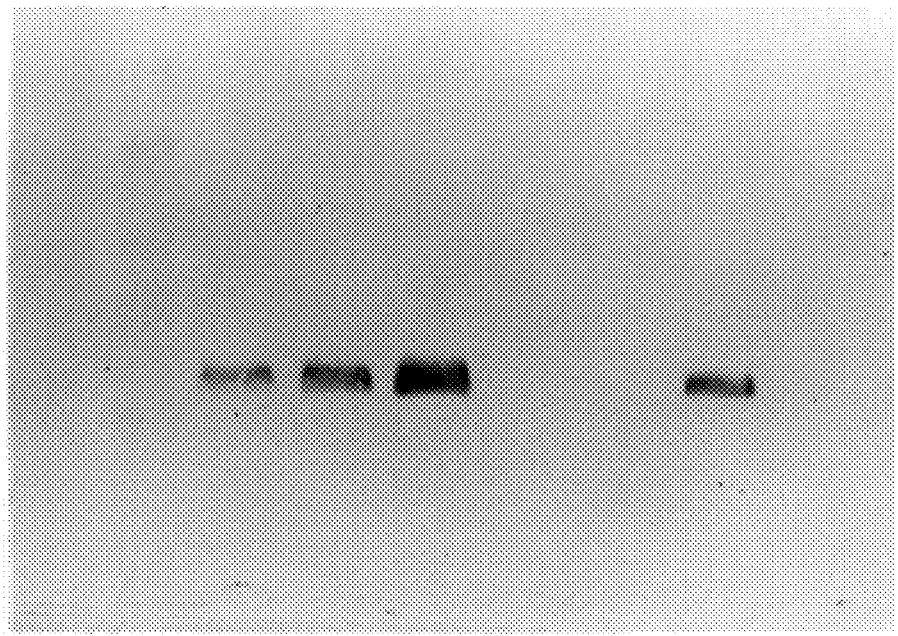

FIG. 7C shows the cross-reactive proteins of EPEC which react with the anti-haemophilus adhesin antibodies. Lanes 1 and 2 are the water extracts of EPEC E2348. Lane 3 is EPEC boiled in SDS. Lanes 4 and 5 are the water extracts of the non-pathogenic HB101 *E. coli*. Lane 6 is the SDS extract of HB101.

Figure 7D:
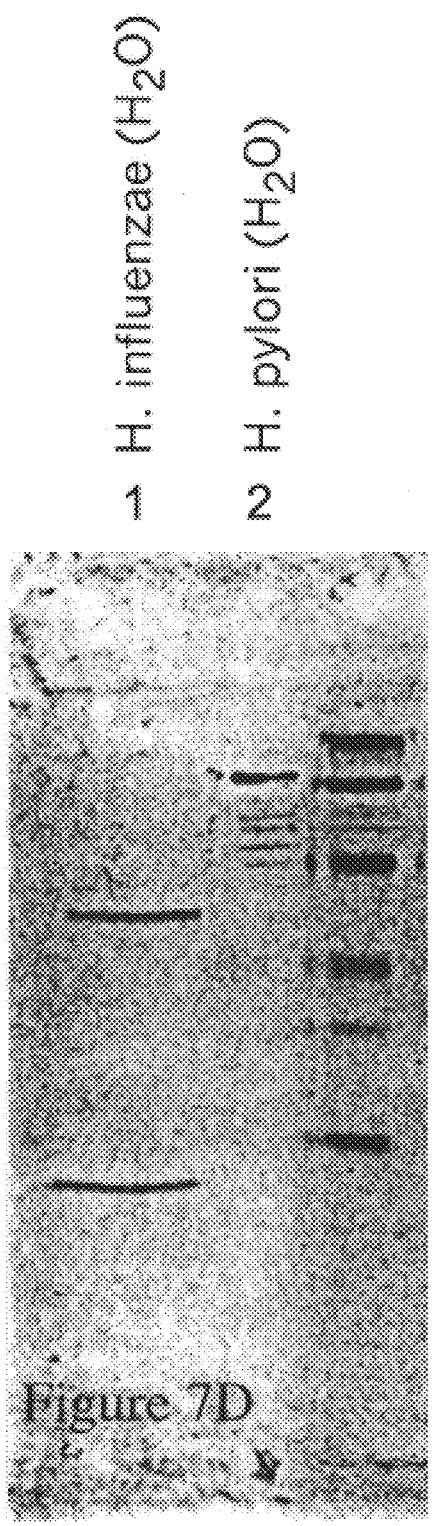

FIG. 7D shows cross-reactivity with *H. pylori*. Lane 1 is a western blot of a water extract of *Haemophilus influenzae* and lane 2 is a water extract of *Helicobacter pylori*.

DETAILED DESCRIPTION OF THE INVENTION

In accordance with one aspect of the invention, a surface adhesin protein can be isolated from any strain of *H. influenzae*.

The adhesin protein may be isolated and purified by PE affinity matrix chromatography as described herein.

In accordance with one embodiment of the invention, the adhesin protein was isolated and purified from *H. influenzae* type b and untypeable serotypes by PE affinity matrix chromatography.

The purified adhesin provides an effective inhibitor of binding of *H. influenzae* organisms to the target glycolipids, PE, $Gg_3$ and $Gg_4$, and of other organisms which bind specifically to these glycolipids. The purified adhesin provides a therapeutic agent which prevents binding of pathogens specific for PE, $Gg_3$ and $Gg_4$ to their target cells.

The isolated and purified adhesin protein was also used to generate anti-adhesin antibodies in rabbits. These antibodies were effective to prevent the binding of *H. influenzae* organisms to the target glycolipids, PE and $Gg_3$, and to mammalian epithelial cells. Anti-adhesin antibodies prepared in accordance with the invention, including monoclonal antibodies, can be used therapeutically, for passive immunisation against diseases caused by *H. influenzae* or can be used for neutralisation of *H. influenzae* organisms.

The common glycolipid recognition pattern among strains of *H. influenzae* means that there is a common expression of adhesin amongst the different strains and additionally that antibodies against the adhesin of the invention are useful with respect to most if not all strains of *H. influenzae*.

The anti-adhesin antibodies of the invention were also effective to prevent the binding of enteropathic *E. coli* (EPEC) organisms to mammalian epithelial cells. These antibodies can be used therapeutically, for passive immunisation against diseases caused by EPEC.

Amino acid sequencing of the N-terminus of the adhesin protein from untypeable *H. influenzae* was performed. The N-terminal sequence of 35 amino acids (SEQ ID NO:4) is shown in bold within the complete amino acid sequence of the adhesin shown in Table 2. This N-terminal sequence was used to search the *H. influenzae* genome database [20] and located an open reading frame of 1011 nucleotides (SEQ ID No:1), shown in Table 1, which encodes a protein of 337 amino acids (SEQ ID NO:2) with a leader sequence of 24 amino acids, shown in Table 2.

Recombinant adhesin protein or a fragment thereof may be prepared by expressing the coding sequence of the adhesin gene or a relevant fragment thereof in an appropriate expression system.

In addition to the disclosed *H. influenzae* adhesin sequence, one of ordinary skill in the art is now enabled to identify and isolate nucleic acids which encode homologous adhesin proteins in other organisms. One of ordinary skill in the art may screen preparations of genomic or cDNA obtained from other organisms or from bacterial or other genomic or cDNA libraries using probes or PCR primers to identify homologous sequences by standard hybridisation screening or PCR techniques.

The purified and isolated DNA molecules comprising at least a portion coding for an adhesin protein of a strain of Haemophilus typified by the embodiments described herein are advantageous as nucleic acid probes for the identification of unique sequences found in different strains of haemophilus and for the identification of haemophilus infection; the products encoded by the DNA molecules are useful as antigens for the production of Haemophilus-specific antisera and for vaccination against the diseases caused by Haemophilus.

The adhesin encoded by the nucleic acid molecules of the present invention, fragments and analogs thereof, and peptides containing sequences corresponding to portions of the adhesin that are conserved between various isolates of Haemophilus and other bacteria that produce the adhesin, are useful in diagnosis of and immunisation against diseases caused by any bacterial strain that produces the adhesin protein, or an adhesin protein of similar binding specificity.

The various embodiments of the present invention enable many applications for treatment of and vaccination against infections with *H. influenzae*, or with other bacterial pathogens, including *E. coli* and *H. pylori*, which produce an adhesin which binds specifically to PE, $Gg_3$ and $Gg_4$ and enable immunological reagents for use in these applications.

Some examples of these applications are discussed below, although the invention is not limited to these examples.

1. Vaccine Preparation and Use

Immunogenic compositions, suitable to be used as vaccines, may be prepared from immunogenic adhesin protein, analogues and fragments thereof and/or peptides as disclosed herein. Such immunogenic compositions elicit an immune response in a treated subject which produces antibodies, including anti-adhesin antibodies and antibodies that are opsonizing or bactericidal. If the treated subject is challenged by *H. influenzae* or other bacteria that produce an adhesin, the antibodies elicited by the vaccination bind to the invading organism and prevent binding of the organism to susceptible cells of the subject. Opsonizing or bactericidal antibodies may also provide protection by alternative mechanisms.

Vaccines containing proteins or peptides are generally well known in the art, as exemplified by U.S. Pat. Nos. 4,601,903; 4,599,231; 4,599,230; and 4,596,792; all of which references are incorporated herein by reference. Immunogenic compositions including vaccines may be prepared as injectables, as liquid solutions or emulsions. The adhesin protein, analogues and fragments thereof and/or peptides may be mixed with pharmaceutically acceptable excipients which are compatible with the adhesin protein, fragments, analogues or peptides. Such excipients may include water, saline, dextrose, glycerol, ethanol, and combinations thereof. The immunogenic compositions and vaccines of the invention may further contain auxiliary substances such as wetting or emulsifying agents, pH buffering agents, or adjuvants to enhance the effectiveness of the vaccines. Immunogenic compositions and vaccines may be administered parenterally, or by injection subcutaneously or intramuscularly. Alternatively, the immunogenic compositions formed according to the present invention may be formulated and delivered in a manner to evoke an immune response at mucosal surfaces. Thus, the immunogenic composition may be administered to mucosal surfaces by, for example, the nasal or oral routes. The immunogenic compositions of the invention may be provided in combination with a targeting molecule for delivery to specific cells of the immune system or to mucosal surfaces. Some such targeting molecules including strain B12 and fragments of bacterial toxins, as described in WO92/17167 (Biotech Australia Pty. Ltd.), and monoclonal antibodies, as described in U.S. Pat. No. 5,194,254 (Barber et al.). Alternatively, other modes of administration including suppositories and oral formulations may be desirable. For suppositories, binders and carriers may include, for example, polyalkalene glycols or triglycerides. Oral formulations may include normally employed excipients such as, for example, pharmaceutical grades of saccharine, cellulose and magnesium carbonate. Immunogenic compositions may take the form of solutions, suspensions, tablets, pills, capsules, sustained release formulations or powders and may comprise 10–95% of the adhesin protein, analogues and/or peptides.

The vaccines are administered in a manner compatible with the dosage formulation, and in such amount as will be therapeutically effective, protective and immunogenic. The quantity of vaccine to be administered depends on the subject to be treated, including, for example, the weight of the subject and the capacity of the subject's immune system to synthesise antibodies, and if needed, to produce a cell-mediated immune response. The dosage of the vaccine may also depend on the route of administration. However, suitable dosage ranges are readily determinable by one skilled in the art and may be of the order of micrograms of the adhesin protein, analogues and fragments thereof and/or peptides. Suitable regimes for initial administration and booster doses of vaccine are also well known in the art. These include an initial administration followed by subsequent administrations.

The nucleic acid molecules encoding the adhesin protein of the present invention may also be used for immunisation, by administration of the DNA directly, for example by injection for genetic immunisation or by constructing a live vector such as Salmonella, BCG, adenovirus, poxvirus, vaccinia or poliovirus including the DNA. Some live vectors that have been used to carry heterologous antigens to the immune system are discussed in, for example, O'Hagan (24). Processes for the direct injection of DNA into subjects for genetic immunisation are described in, for example, Ulmer et al. (25).

The immunogenicity of antigens can be significantly improved if they are co-administered with adjuvants.

Adjuvants or immunostimulatory agents are known to improve host immune responses to vaccines. Intrinsic adjuvants, such as lipopolysaccharides, normally are the components of the killed or attenuated bacteria used as vaccines. Aluminum hydroxide and aluminum phosphate (collectively commonly referred to as alum) are adjuvants commonly used in human and veterinary vaccines.

An adjuvant should be non-toxic, capable of stimulating a sustained immune response and compatible with the immunogenic composition employed as a vaccine.

U.S. Pat. No. 4,855,283 granted to Ockhoff et al. on Aug. 8, 1989 which is incorporated herein by reference teaches glycolipid analogues, including N-glycosylamides, N-glycosylureas and N-glycosylcarbamates, each of which is substituted in the sugar residues by an amino acid, as immuno-modulators or adjuvants. Lockhoff et al. (26) reported that N-glycolipid analogues displaying structural similarities to the naturally-occurring glycolipids, such as glycosphingolipids and glycoglycerolipids, are capable of eliciting strong immune responses both to herpes simplex virus and to pseudorabies virus. Some glycolipids have been synthesised from long chain-alkylamines and fatty acids that are linked directly with the sugars through the anomeric carbon atom, to mimic the functions of the naturally occurring lipid residues.

Lipidation of synthetic peptides has also been used to increase their immunogenicity. Thus, Wiesmuller (27), describes a peptide with a sequence homologous to a foot-and-mouth disease viral protein coupled to an adjuvant tripalmityl-s-glyceryl-cysteinylserylserine, being a synthetic analogue of the N-terminal part of the lipoprotein from Gram negative bacteria. Furthermore, Deres et al. (28), reported in vivo priming of virus-specific cytotoxic T lymphocytes with synthetic lipopeptide vaccine which comprised modified synthetic peptides derived from influenza virus nucleoprotein by linkage to a lipopeptide, N-palmityl-s-[2,3-bis(palmitylxy)-(2RD)-propyl-[R]-cysteine (TPC).

2. Expression of Adhesin Gene

With the knowledge of the gene sequence encoding adhesin, probes and primers may be constructed and used to detect the 46 kDa protein. Probes may be composed of DNA, RNA, nucleic acid analogues or any combination. The length of the probe may be as few as 12 nucleotides or as large as the coding sequence for the protein. Probes may be constructed and labeled using techniques which are well known in the art. Short probes may be generated synthetically while longer probes may be generated by PCR amplification in the presence of labeled precursors. Probes may be labeled by a variety of markers including radioactive, fluorescent, enzymatic and chromogenic. As mentioned, probes may be utilized to detect the presence of the adhesin protein in a variety of samples providing a means for detection of this protein.

The adhesin gene sequence may be manipulated to understand the expression of the gene and gene product. Alternatively, cell lines may be produced which overexpress the gene product allowing purification of adhesin for biochemical characterization, large-scale production, antibody production and patient therapy.

For protein expression, eukaryotic and prokaryotic expression systems may be generated in which the adhesin gene sequence is introduced into a plasmid or other vector which is then introduced into living cells. Constructs in which the adhesin cDNA sequence containing the entire open reading frame is inserted in the correct orientation into an expression plasmid may be used for protein expression. Alternatively, portions of the sequence may be inserted. Prokaryotic and eukaryotic expression systems allow various important functional domains of the protein to be recovered as fusion proteins and used for binding, structural and functional studies and also for the generation of appropriate antibodies.

Typical expression vectors contain promoters that direct the synthesis of large amounts of mRNA corresponding to the gene. They may also include sequences allowing for their autonomous replication within the host organism, sequences that encode genetic traits that allow cells containing the vectors to be selected, and sequences that increase the efficiency with which the mRNA is translated. Stable long-term vectors may be maintained as freely replicating entities by using regulatory elements of viruses. Cell lines may also be produced which have integrated the vector into the genomic DNA and in this manner the gene product is produced on a continuous basis.

Expression of foreign sequences in bacteria such as *E. coli* require the insertion of the sequence into an expression vector, usually a plasmid which contains several elements such as sequences encoding a selectable marker that assures maintenance of the vector in the cell, a controllable transcriptional promoter which upon induction can produce large amounts of mRNA from the cloned gene, translational control sequences and a polylinker to simplify insertion of the gene in the correct orientation within the vector. A relatively simple *E. coli* expression system utilizes the lac promoter and a neighboring lacZ gene which is cut out of the expression vector with restriction enzymes and replaced by the adhesin gene sequence. In vitro expression of proteins encoded by cloned DNA is also possible using the T7 late-promoter expression system. Plasmid vectors containing late promoters and the corresponding RNA polymerases from related bacteriophages such as T3, T5 and SP6 may also be used for in vitro production of proteins from cloned DNA. *E. coli* can also be used for expression by infection with M13 Phage mGPI-2. *E. coli* vectors can also be used with phage lambda regulatory sequences, by fusion protein vectors, by maltose-binding protein fusions, and, by glutathione-S-transferase fusion proteins.

Eukaryotic expression systems permit appropriate post-translational modifications to expressed proteins. This allows for studies of the adhesin gene and gene product including determination of proper expression and post-translational modifications for biological activity, identifying regulatory elements in the 5' region of the gene and their role in tissue regulation of protein expression. It also permits the production of large amounts of normal proteins for isolation and purification, to use cells expressing adhesin as a functional assay system for antibodies generated against the protein, to test the effectiveness of pharmacological agents or as a component of a signal transduction system to study the function of the normal complete protein, specific portions of the protein, or of naturally occurring polymorphisms and artificially produced mutated proteins.

The adhesin DNA sequence can be altered using procedures such as restriction enzyme digestion, DNA polymerase fill-in, exonuclease deletion, terminal deoxynucleotide transferase extension, ligation of synthetic or cloned DNA sequences and site-directed sequence alteration using specific oligonucleotides together with PCR.

Once the appropriate expression vector containing the adhesin gene is constructed, it is introduced into an appropriate E. coli strain by transformation techniques including calcium phosphate transfection, DEAE-dextran transfection, electroporation, microinjection, protoplast fusion and liposome-mediated transfection.

The host cell which may be transfected with the vector of this invention may be selected from the group consisting of E. coli, Pseudomonas, Bacillus subtilis, or other bacilli, other bacteria, yeast, fungi, insect (using baculoviral vectors for expression), mouse or other animal or human tissue cells. Mammalian cells can also be used to express the adhesin protein using a vaccinia virus expression system.

The cellular distribution of adhesin in tissues can be analyzed by reverse transcriptase PCR analysis. Antibodies can also be generated for several applications including both immunocytochemistry and immunofluorescence techniques to visualize the protein directly in cells and tissues in order to establish the cellular location of the protein.

3. Anti-adhesin Antibodies

In order to prepare polyclonal antibodies, fusion proteins containing defined portions or all of the adhesin protein can be synthesized in bacteria by expression of corresponding DNA sequences in a suitable cloning vehicle. Fusion proteins are commonly used as a source of antigen for producing antibodies. Two widely used expression systems for E. coli are lacZ fusions using the pUR series of vectors and trpE fusions using the pATH vectors. The protein can then be purified, coupled to a carrier protein if desired, and mixed with Freund's adjuvant (to help stimulate the antigenic response of the animal) and injected into rabbits or other appropriate laboratory animals. Alternatively, the protein can be isolated from adhesin protein-expressing cultured cells. Following booster injections at weekly intervals, the rabbits or other laboratory animals are then bled and the sera isolated. The sera can be used directly or purified prior to use by various methods including affinity chromatography employing Protein A-Sepharose, Antigen Sepharose or Anti-mouse-Ig-Sepharose. The sera can then be used to probe protein extracts from cells and tissues run on a polyacrylamide gel to identify the adhesin protein. Alternatively, synthetic peptides can be made to the antigenic portions of the protein and used to inoculate the animals.

The most common practice is to choose a 10 to 15 residue peptide corresponding to the carboxyl or amino terminal sequence of a protein antigen and to chemically cross-link it to a carrier molecule such as keyhole limpet haemocyanin or BSA. However, if an internal sequence peptide is desired, selection of the peptide is based on the use of algorithms that predict potential antigenic sites. These predictive methods are, in turn, based on predictions of hydrophilicity (Kyte and Doolittle (29), Hopp and Woods (30)) or secondary structure (Chou and Fasman (31)). The objective is to choose a region of the protein that is either surface exposed such as a hydrophilic region or a region conformationally flexible relative to the rest of the structure, such as a loop region or a region predicted to form a β-turn. The selection process is also limited by constraints imposed by the chemistry of the coupling procedures used to attach peptide to carrier protein. A carboxyl-terminal peptide is chosen because they are often more mobile than the rest of the molecule and the peptide can be coupled to a carrier in a straightforward manner using glutaraldehyde. The amino-terminal peptide has the disadvantage that it may be modified post-translationally by acetylation or by the removal of a leader sequence. A comparison of the protein amino acid sequence between species can yield important information. Those regions with sequence differences are likely to be immunogenic. Synthetic peptides can also be synthesized as immunogens as long as they mimic the native antigen as closely as possible.

It is understood by those skilled in the art that monoclonal adhesin antibodies may also be produced using adhesin protein obtained from cells actively expressing the protein or by isolation from tissues. The cell extracts, or recombinant protein extracts, containing the adhesin protein, are injected in Freund's adjuvant into mice. After being injected 9 times over a three week period, the mice spleens are removed and resuspended in phosphate buffered saline (PBS). The spleen cells serve as a source of lymphocytes, some of which are producing antibody of the appropriate specificity. These are then fused with a permanently growing myeloma partner cell, and the products of the fusion are plated into a number of tissue culture wells in the presence of a selective agent such as HAT. The wells are then screened by ELISA to identify those containing cells making binding antibody. These are then plated and after a period of growth, these wells are again screened to identify antibody-producing cells. Several cloning procedures are carried out until over 90% of the wells contain single clones which are positive for antibody production. From this procedure a stable line of clones which produce the antibody is established. The monoclonal antibody can then be purified by affinity chromatography using Protein A Sepharose, ion-exchange chromatography, as well as variations and combinations of these techniques. Truncated versions of monoclonal antibodies may also be produced by recombinant techniques in which plasmids are generated which express the desired monoclonal antibody fragment(s) in a suitable host. Antibodies specific for mutagenic epitopes can also be generated.

The adhesin protein, analogues and fragments thereof and/or peptides of the invention are also useful as antigens in immunoassays including enzyme-linked immunosorbent assays (ELISA), radioimmunoassays (RIA) and other non-enzyme linked antibody binding assays or procedures known in the art for the detection of the protein.

EXAMPLES

The examples are described for the purposes of illustration and are not intended to limit the scope of the invention.

Methods of molecular genetics, protein and peptide biochemistry and immunology referred to but not explicitly described in this disclosure and examples are reported in the scientific literature and are well known to those skilled in the art.

Materials

PE from Escherichia coli, PE from soybean, phosphatidylinositol [PI], bovine brain SGC and galactosylceramide [GC] were purchased from Sigma. $Gg_4$ was made by desialating GM1, and gangliosides (GM3, GM2, GM1, GT1a/b, and GD1a/b] were prepared from bovine brain tissue. $Gg_3$ was prepared from guinea pig blood [18], and lactosylceramide [LC], globotriaosylceramide [$Gb_3$] and globotetraosylceramide [$Gb_4$] from human kidney tissue by silica gel chromatography [19]. Plastic-backed silica gel (SILG) tlc plates were from Brinkmann. Goat anti-rabbit horseradish peroxidase conjugate was from Bio-Rad. Polyclonal anti-H. influenzae antibody was from Biodesign Int. $Na^{125}I$ was purchased from Amersham. The nasopharyngeal epithelial tumour cell line, HEp-2, and clinical strains of H. influenzae were provided and serotyped by the Dept. of Microbiology, Hospital for Sick Children. These strains were isolated from blood cultures of autopsies and patients with acute lymphoblastic leukemia, prenatal asphyxia, fever, premature birth, urinary tract infection, sudden infant death syndrome, abdominal pain, leg infection, sepsis and CSF culture of meningitis following shunt malfunction in a brain tumour patient. Enteropathic *E. Coli* strain 2348 (serotype 0127H6) was also obtained from ATCC, Maryland, U.S.A.

Example 1

Purification of Adhesin

Thirteen clinical strains of *Haemophilus influenzae*, including types b, d and untypeable, were provided by the Department of Microbiology, Hospital for Sick Children. Strains were plated from frozen stocks on to Chocolate agar plates, and grown overnight in a $CO_2$ incubator at 37° C. Each strain was plated 3 times prior to use in an assay.

Tlc overlay. A mixture of glycolipid standards, PI and a pure preparation of soybean PE (3 μg of each species) were separated by tlc with chloroform-methanol-0.88% aqueous KCl (60:40:9 vol/vol). Following this, the plates were either: (1) stained with orcinol (to detect glycolipids), with molybdenum blue (to detect phospholipids), or ninhydrin (to detect free amines); or (2) the plates were dried and blocked by incubation with 3% gelatin in 100 mM Tris-buffered saline (TBS) for 2 hrs at 37° C., incubated with approximately $5×10^8$ *H. influenzae* in 100 mM TBS under aerobic conditions via gentle shaking for 2 hrs at room temperature, and binding of *H. influenzae* was detected immunologically [10, 20].

All thirteen strains specifically recognised soybean phosphatidyl ethanolamine (PE), gangliotetraosylceramide ($Gg_4$), gangliotriosylceramide ($Gg_3$), sulfatoxygalactosylceramide (SGC), and to a lesser extent sulfatoxygalactosylglycerol (SGG) (data not shown). Of the multiple lipids screened, only these lipids were strongly recognised.

Preparation of affinity matrix. Glycolipid-ligand interactions are most simply demonstrated by the tlc overlay procedure [21]. This procedure involves detection of a ligand bound to a carbohydrate (glycolipid) receptor immobilized on a silica gel tlc plate. This principle was used to develop a convenient means of generating any glycolipid (or lipid) affinity matrix by merely adsorbing the lipid receptor onto silica [22].

Briefly, 50 mg of PE (from *E. coli*) in 50 ml of methanol was mixed and vortexed with 20 g of activated Celite 545. The methanol was evaporated using a rotovaporator. The PE matrix was suspended in 100 mM TBS, and added to a column and blocked by running through 50 ml of 1% glycine at room temperature. The gel was washed with 100 ml of 100 mM TBS at 4° C. prior to use.

Purification of *H. influenzae* adhesin. A representative type b strain and an untypeable clinical strain of *H. influenzae* were grown on 80 chocolate agar plates. The bacteria was resuspended with cotton swabs in 10 mM PBS (5 ml/sterile falcon tube) and spun down at 3500 rpm for 15 min. The supernatant was discarded and the washing step repeated. The pellet was resuspended in 1–2 ml water and the suspension was transferred to eppendorf caps. The suspension was vortexed for 1 minute at the highest speed and then spun down 5 minutes at 14000 rpm in the microcentrifuge. Finally, the supernatant was filtered 2× using a 0.45 μfilter [23, 24].

Approximately 80 ml of water extract (2 mg/ml of protein) in 1 mM phenylmethylsulfonyl fluoride at 4° C. was applied to the PE affinity matrix at a flow rate of approximately 0.5 ml/min. The column was washed out with 2 L of 100 mM TBS to remove the unbound proteins. Bound protein was eluted with 400 ml of an EDTA gradient (5 mM to 10 mM), and then with 200 ml of 1M TRIS (pH 10.5). No PE was found in the washing or elution buffers. The eluted protein was dialyzed against 10 mM TBS at 4° C. and lyophilized. The protein was then separated by SDS-PAGE and stained with Coomassie blue.

The column elution resulted in two preparations. The eluate with EDTA consisted of a single protein with a molecular mass of approximately 46 kDa (FIG. 1, Lane C). The Tris eluate consisted of several proteins with a dominant species of approximately 46 kDa. A species of the same apparent molecular mass was purified by PE affinity chromatography/EDTA elution from both type b and untypeable *H. influenzae* (FIG. 1, lanes C and D).

Example 2

Inhibition of Binding of *H. influenzae* to Receptor $I^{125}$ labeling of *H. influenzae*. Cultured *H. influenzae* was harvested and suspended in 100 mM TBS at a concentration of $10^9$ bacteria per ml. The cells were centrifuged at 2000 rpm for 10 min. to remove any loose membrane components. The cells were suspended in an iodogen-coated eppendorf tube and reacted with 1 mCi of $I^{125}$ per 0.5 ml of suspension for 10 min. at 4° C., and 5 min. at room temperature [25]. The labelled cells were then transferred to a new eppendorf tube, washed 3 times with 100 mM TBS, and suspended at a final concentration of $10^8$ bacteria per ml.

Water extraction of proteins. Bacteria were scraped from agar plates with cotton swabs and suspended in 10 mM PBS (5 ml/sterile falcon tube). Bacteria were spun down at 3500 rpm for 15 min, washed again once and resuspended in 1–2 ml water by vortexing for 1 min. at maximum speed. Cells were then removed by centrifuging for 5 min at 14000 rpm and the supernatant water extract was filter twice (0.45μ filter). All operations were carried out at room temperature.

Microtitre binding assay. PE from soybean, $Gg_3$ or $Gb_4$ were separately mixed with cholesterol and phosphatidylcholine (PC) in a ratio of 1 μg:0.1 μg in 50 μl of methanol [18]. A solution of cholesterol and PC in a ratio of 0.1 μg:0.1 μg was also prepared in 50 μl of methanol as a control. Wells of flat-bottom microtitre plates were coated with each receptor lipid mixture by air drying at room temperature overnight. Non-specific binding sites were blocked with 100 μl of 3% gelatin for 1 hr at 37° C. After washing with 100 mM TBS, the wells were incubated for 40 min. with 100 μl of either 100 mM TBS, or with serial dilutions of potential inhibitors including unlabelled *H. influenzae* organisms, water-extracted proteins, or the affinity-purified adhesin. The plate wells were then washed and incubated for 2 hrs with $10^7$ $I^{125}$ -*H. influenzae* organisms. The plates were washed, dried and individual wells cut out and counted in a gamma counter.

Figure 2A:
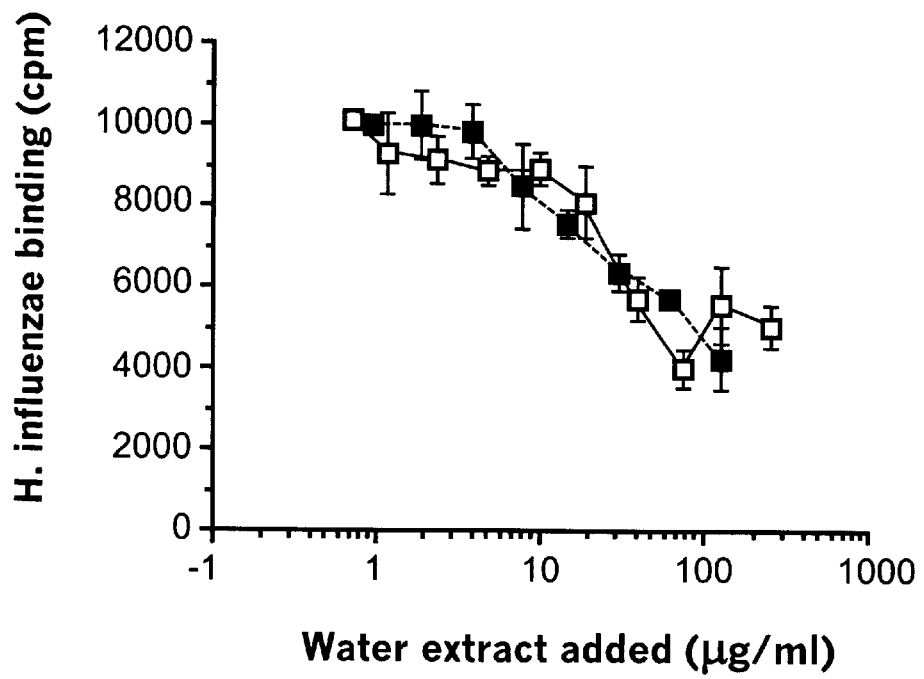

FIG. 2A shows inhibition of binding of $^{125}$I-*H. influenzae* organisms to PE by water extracted proteins from *H. influenzae*. Background binding of *H. influenzae* to globotetraosylceramide was routinely <500 cpm.

Figure 2B:
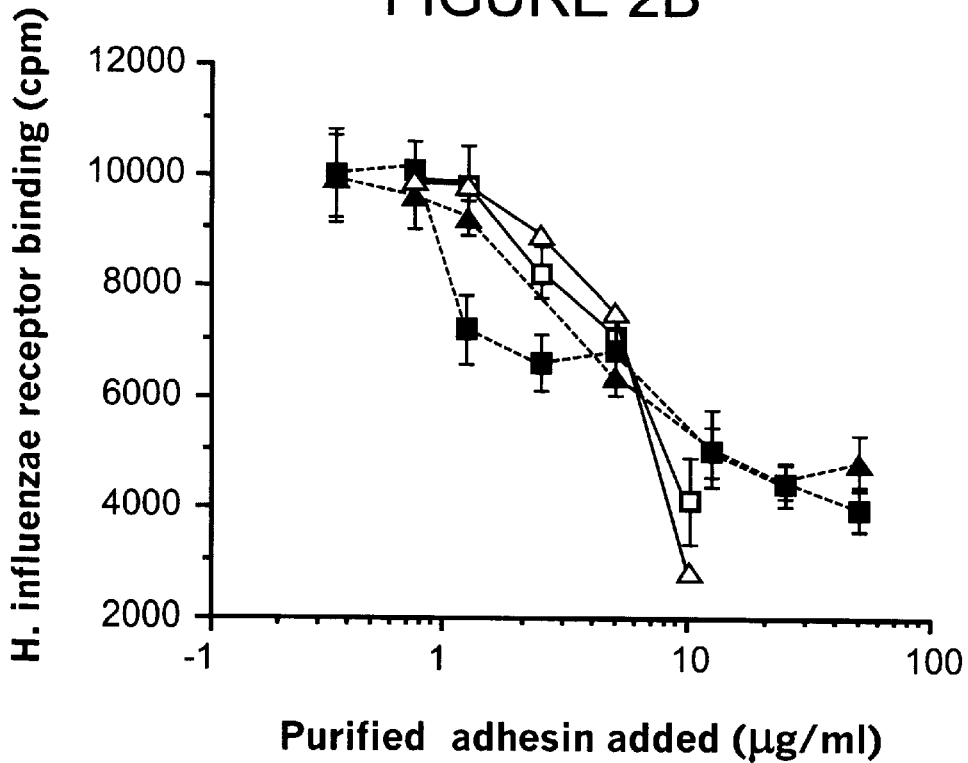

Specific binding of both *H. influenzae* type b or untypeable to PE and $Gg_3$ was established (FIG. 2). In comparison, *H. influenzae* binding to $Gb_4$ for example, in the Relisa format, as for the tlc overlay was not above background. In order to determine the maximum inhibition possible, binding was inhibited by using unlabelled whole cells (data not shown), and secondly by using water-extracted surface proteins (FIG. 2A). Both for unlabelled intact organism (not shown) and for water extracted proteins, maximum inhibition was approximately 65% (corresponding to $10^6$ bacteria per ml or 100 μg/ml of surface proteins). The purified adhesin was found to achieve this level of inhibition of binding (60–70%) to either receptor, at a concentration of 10 μg/ml, irrespective of serotype (FIG. 2B).

Example 3
Preparation of Anti-Adhesin Antibody

Anti-*H. influenzae* PE-binding adhesin antibody. A new Zealand white rabbit was bled (10 ml) to obtain pre-immune serum, and then inoculated with approximately 50 μg in PBS of *H. influenzae* adhesin, purified from untypeable *H. influenzae* as described in Example 1. Two subsequent injections were administered of 50 μg of adhesin in PBS separated by intervals of three weeks. The rabbit was then bled after a third 3 week period, and the serum was harvested and tested for sensitivity against the adhesin by Western blotting.

Western blotting. A semi-pure preparation of the untypeable *H. influenzae* PE binding adhesin (500 ng), and the water-extracted surface proteins of untypeable *H. influenzae* (2 μg) were separated via SDS-PAGE, and transferred to nitrocellulose [22]. The resulting blot was then blocked with 3% gelatin at 37° C. for 2 hours, washed 3 times with a solution of 0.1% gelatin and 0.025% Tween 20 in 10 mM TBS, and reacted with a 1:500 dilution of the polyclonal anti-PE binding adhesin of untypeable *H. influenzae* overnight at 4° C. A washing step followed, and the blot was incubated with a 1:2000 dilution of goat anti-rabbit antibody conjugated with horseradish peroxidase for 2 hours at room temperature. Binding was detected with the addition of 4-chloro-1-naphthol.

Detection of *H. influenzae* adhesin by Western Blot. Four clinical *H. influenzae* isolates were extracted with water or boiled in sample buffer, separated by SDS PAGE and immunostained with 0.2% anti-adhesin serum.

Antisera raised against the adhesin recognized one major species (MW ca 45 kDa) in the water extract of several *H. influenzae* clinical isolates (FIG. 3, panel 1). Some minor variation in size was observed from strain to strain. In total cell extracts, a second major immunoreactive species was also detected (MW>20 kDa) (FIG. 3, panel 2). Minor cross reactive species were detected at 90 and 30 kDa in both extracts.

Example 4
Inhibition of *H. influenzae*/HEp-2 Cell Binding By Anti-Adhesin Antibody $10^8$ *H. influenzae* untypeable whole cells were preincubated for 1 hour at room temperature with various concentrations of adhesin-specific antiserum or preimmune serum or with 10 mM PBS. The mixtures were then added to confluent HEp-2 cells (approximately 250,000 cells) in 12 well plates [23] and incubated for 3 hours at 37° C. in 5% $CO_2$. The wells were washed 5 times with 10 mM PBS, and the cells removed via trypsinization. The trypsin was inactivated with fetal calf serum and the cells were spun down and lysed with water. The lysate was plated out in serial dilutions onto chocolate agar plates and left to grow overnight at 37° C. The colonies were counted, and averages were determined from at least triplicate determinations. The results are shown in FIG. 4.

The binding of *H. influenzae* to HEp-2 cells was found to decrease by approximately 50% when bacteria were pre-incubated with a 1:50 dilution of the anti-*H. influenzae* PE binding adhesin antibody, and by approximately 60% following pre-incubation of either a 1:20 or a 1:10 dilution. Pre-incubation of *H. influenzae* with equivalent dilution of preimmune serum resulted in no significant inhibition of binding to HEp-2 cells (FIG. 4).

Example 5
Inhibition of *H. influenzae*/PE and $Gg_3$ Binding By Anti-Adhesin Antibody Binding of *H. influenzae* organisms to PE or $Gg_3$ after incubation of the organism with anti-adhesin antibody was examined by the tlc overlay method described in Example 1.

Preincubation of *H. influenzae* with the anti-adhesin serum resulted in the complete loss of the ability of the organism to bind to PE or $Gg_3$ as monitored by tlc overlay (FIG. 5, lanes B, E and G), whereas binding was retained for organisms preincubated with immune serum raised against the whole organism (lane C) or nonimmune serum (lanes A, D and F).

Example 6
Identification of the *H. influenzae* Adhesin Gene

A sample of adhesin purified from untypeable *H. influenzae* by the method described in Example 1 was subjected to N-terminal amino acid sequencing and thirty five amino acids were identified, as follows:

VLASVKPLGFIVSSIADGVTGTQVLVPAGASPHDY (SEQ ID NO:4)

V L A S K V K P L G F I V S S I A D G V T G T Q V-LVPAGASPHDY

This sequence was searched for in the TIGR *H. influenzae* type b genome database [20].

An open reading frame containing this sequence with 100% identity was located, encoding a protein of 337 amino acids with a 24 amino acid leader sequence. The complete nucleic acid sequence is shown in Table 1 and the deduced amino acid sequence is shown in Table 2.

Example 7
Inhibition of EPEC/HEp-2 Cell Binding by Anti-*H. influenzae* Adhesin Antibody Enteropathic *E. coli* (EPEC) whole cells were preincubated for 1 hour at room temperature with various concentrations of anti-*H. influenzae* adhesin-specific antiserum or preimmune serum or with PBS.

The mixtures were then added to confluent HEp-2 cells and EPEC binding was determined as described in Example 4.

The results are shown in FIG. 6 and demonstrate that anti-*H. influenzae* adhesin antibody can inhibit binding of EPEC cells to HEp-2 cells.

Example 8
Cross-Reactivity of Anti-Adhesin Antibodies With EPEC and *H. pylori*

The experimental protocols were as those described in example 3.

Extracts of HB101, GST-adhesin recombinant fusion protein of haemophilus, extract of EPEC, water extract of EPEC and bound and eluted material of EPEC extract were run on a gel, transferred to nitrocellulose and incubated in the presence of anti-haemophilus adhesin antibodies to identify the cross-reactive proteins. This is shown in FIG. 7A. Lane 1 shows the water surface extract of HB101, a non-pathogenic lab *E. coli* strain. Lane 2 shows reactivity with the GST-adhesin recombinant protein of haemophilus. Lane 3 and lane 4 shows the reactivity of water extract of the EPEC strain E2348. Lane 5 shows the water extract from E2348 which was unbound on a PE column. Lane 6 shows the material that was bound and eluted from a PE column.

FIG. 7B shows the results from affinity purification of the cross-reactive protein from EPEC. Lanes 1 and 2 show the unbound fraction. Lanes 3 and 4 show the sodium chloride eluted material from the PE column. Lanes 5 and 6 shown the Tris pH10 eluate from the PE column. The cross-reactive 20 kDa band is eluted under high pH conditions.

FIG. 7C shows the cross-reactive proteins of EPEC which react with the anti-haemophilus adhesin antibodies. This gel illustrates that the cross-reactive protein is present in the surface extract of the pathogenic strain E2348 but is not present in the surface extract of the non-pathogenic HB101. The cross-reactive protein is expressed in HB101 inside the bacterium and is only released on boiling with SDS. Lanes 1 and 2 are the water extracts of EPEC E2348. Lane 3 is EPEC boiled in SDS. Lanes 4 and 5 are the water extracts of the non-pathogenic HB101 *E. coli*. Lane 6 is the SDS extract of HB101.

FIG. 7D shows cross-reactivity with *H. pylori*. Lane 1 is the western blot of the water extract of the *Haemophilus influenzae* and lane 2 is the water extract from *Helicobacter pylori*.

Example 9
Blocking of *H. Pylori* Binding to Lipids By Anti-*H. Influenzae* PE-Binding Adhesin

*H. pylori* suspension was prepared by re-suspending the strain LC11, grown on skirrow's medium blood agar plates for 3 days under reduced oxygen conditions ($CO_2$, 10%; $O_2$, 5%; $N_2$, 85%) at 37° C., in 100 mM tricine-buffered saline (TBS) pH 7.5.

5 μg of PE, $Gg_3$ and $Gg_4$ were separated by TLC in 2, 3×7 cm plastic-backed silica thin layer plates (Polygram SilG), with chloroform/methanol/water (5/4/1). Nonspecific binding sites on the TLC plates were blocked by incubating for 2 hours at 37° C. with 2% gelatin from bovine skin (type B/Sigma), washed with water and overlaid with 10 ml aliquots of the *pylori* suspension ($10^7$ bacteria/ml); pre-incubated with: a) a nonimmune rabbit sera, b) a polyclonal anti-PE-binding adhesin from *H. Influenzae*, both at final protein concentration of 0.2 mg/ml. Preincubation was for 30 minutes and overlay for 2 hours, both under reduced oxygen conditions at 37° C., plates were extensively washed with TBS.

*H. pylori* bound to lipids was detected by using an anti-*H. pylori* rabbit antiserum and secondary goat anti-rabbit antibodies coupled with peroxidase.

These experiments indicated that anti-adhesin pretreatment prevented *H. pylori* binding to $Gg_3$, $Gg_4$ and PE whereas nonimmune serum had no effect.

Example 10
Expression of Adhesin from *Haemophilus influenzae*

The 939 bp coding sequence of the adhesin gene was amplified by PCR. The PCR product was subcloned into GST fusion protein vector pGEX-2T and 6×His tag fusion protein vector pTrcHis-A. Recombinant adhesins were expressed in *E. coli* as GST-Adhesin and 6×His-Adhesin, respectively. GST-Adhesin was purified by Ni-NTA column under denaturing conditions. Both fusion proteins also could be purified on a PE affinity column, and recognized by polyclonal anti-adhesin antibody in western blot. As monitored by TLC overlay, both fusion proteins bind to Gg3, Gg4, but do not bind to GM1, Gb3 and Gb4. GST-Adhesin also binds to soybean PE and PE from Hep2 cells, but does not bind to PC. A C-terminal truncated mutant was also made by deleting the C-terminal 231 bp. This mutant lost PE binding capacity but retained Gg4 binding. This indicates that the C-terminus of the adhesin is very important for PE binding and that the binding site for Gg4 may be different from the PE binding site.

The present invention is not limited to the features of the embodiments described herein, but includes all variations and modifications within the scope of the claims.

REFERENCES

1. Smith et al., (1989), *Haemophilus influenzae*, Baltimore: Williams & Wilkins, 242–244.
2. Korones et al., (1992), *Ped Infect Dis J.*, 11:516–520.
3. Moxon E R. Principals and practices of infectious diseases. In: G. M, R. D. and J. B. *Haemophilus influenzae*. New York: Wiley Medical Publications, (1989) 1722–1729.
4. Dimmock, N. J., (1982), *J. Gen. Virol.*, 59:1–22.
5. McClintock P R, (1988), Concepts in viral pathogenesis. In: Notkins A L and Oldstone M B A, "Viral receptors: expression, regulation and relationship to infectivity". New York: Springer-Verlag, 97–101.
6. Sharon et al., (1981), *Ciba Found. Symp.*, 80:119–141.
7. Lingwood C A, (1993), *Helicobacter pylori:* Biology and Clinical Practice. In: Goodwin S and Worsley B. "*H. pylori* adhesins and receptors". CRC Press, Boca Raton, Fla., 209–222.
8. Lingwood et al., (1987), *J Biol Chem*, 262:8834–8839.
9. Lingwood et al., (1991), *Biochem. Biophy. Res. Comm.*, 173:1076–1081.
10. Lingwood et al., (1992), *Infect Immun.*, 60:2470–2474.
11. Jagannatha H. et al., (1991), *Microb. Pathogen.*, 11:259–268.
12. Krivan et al., (1991), *Biochem Biophys Res Commun.*, 175:1082–1089.
13. Yu et al., (1994), *Infect Immun.*, 62:5213–5219.
14. Gupta et al., (1994), *Infect Immun.*, 62:4572–4579
15. Lee et al., (1994), *Mol Microbiol.*, 11:705–713.
16. Zhang et al., (1994), *Infect Immun.*, 62:4367–4373.
17. Brennan et al., (1991) *J Biol Chem.*, 266:18827–18831.
18. Krivan et al., (1988), *Arch. Biochem. Biophys.*, 260:493–496.
19. Lingwood et al., (1993), *Infect Immun.*, 61:2474–2478.
20. Fleischmann, R D., (1995), *Science* 269:496–512.
21. Lingwood et al., (1991), *Biochem Biophys Res Commun.*, 175:1076–1081.
22. Burnette W. N. (1981), *Anal. Biochem.*, 112:195–203.
23. Gold et al., (1993), *Infect Immun.*, 61: 2632–2638.
24. O'Hagan (1992), *Clin. Pharmacokinet*, 22:1.
25. Ulmer et al., (1993). *Curr. Opinion Invest. Drugs*, 2(9): 983.
26. Lockhoff et al., (1991), *Chem. Int. Ed. Engl.*, 30:1611
27. Wiesmuller et al., (1989), *Vaccine*, 8:29.
28. Deres et al., (1989), *Nature*, 342:651.
29. Kyte et al., (1982), *J. Molec. Biol.*, 157:112–122.
30. Hopp et al., (1983), *J. Molec. Biol*, 159:162–165.
31. Chou et al., (1978), *Ann. Rev. Biochem.*, 47:251–276.

TABLE 1 atgaaaaaacttttaaaaattagtgccatttctgccgcacttttaagtgcgccaatgatg gcgaatgccgatgtattagcatcagtaaaacctttaggctttattgtttcatctattgca

TABLE 1-continued

```
gatggcgtaactggtacacaagtccttgttcctgctggcgcctctccgcatgattacaat
ttgaaattatctgatattcaaaaagtaaaatctgcagatttagttgtatggattggtgaa
gacattgattcattcttagacaaaccaattagccaaattgaacgtaaaaaagtgattacc
attgccgatcttgcggatgtaaaacctttattaagtaaagctcaccatgagcatttccat
gaagatggcgatcatgatcatgaccataagcacgaacacaaacatgatcataaacacgac
catgaccatgatcatgatcataaacacgagcataaacacgaccacgaacatcatgatcac
gatcatcacgagggtttaacaacaaactggcacgtttggtattctccagctatcagcaaa
attgttgcacaaaaagtagcggataaattaactgcacaattcccagataaaaaagcgtta
attgcacaaaatctttcagattttaaccgcactttggcagaacaaagtgaaaaaattacg
gcacaacttgcaaatgttaaagataaaggtttctacgttttccacgatgcttatggttat
ttcaacgatgcttatggtttaaaacaaacgggttactttaccatcaatccattagtggca
ccgggtgcaaaaactttagcgcacattaagaagaaattgatgaacataaagtaaattgc
ttattcgcagagcctcaatttacgccaaaagtgattgagtctttagcgaaaaatactaaa
gtcaatgtaggacaactcgacccaattggcgataaagttactttaggtaaaaattcttat
gcaacattcttgcaatctactgcagatagctacatggaatgtttagctaaa
```

TABLE 2

| 1 | MKKLL | KISAI | SAALL | SAPMM | ANADV | LASVK | PLGFI | VSSIA | DGVTG | TQVLV | PAGAS | 5 |
|---|---|---|---|---|---|---|---|---|---|---|---|---|
| 56 | PHDYN | LKLSD | IQKVK | SADLV | VWIGE | DIDSF | LDKPI | SQIERT | KKVIT | IADLA | DVKPL | 110 |
| 111 | LSKAH | HEHFH | EDGDH | DHDHK | HEHKH | DHKHD | HDHDH | DHKHE | HKHDH | EHHDH | DHHEG | 165 |
| 166 | LTTNW | HVWYS | PAISK | IVAQK | VADKL | TAQFP | DKKAL | IAQNL | SDFNR | TLAEQ | SEKIT | 220 |
| 221 | AQLAN | VKDKG | FYVFH | DAYGY | FNDAY | GLKQT | GYFTI | NPLVA | PGAKT | LAHIK | EEIDE | 275 |
| 276 | KHVNC | LFAEP | QFTPK | VIESL | AKNTK | VNVGQ | LDPIG | DKVTL | GKNSY | ATFLQ | STADS | 330 |
| 331 | YEMCL | AK | | | | | | | | | | |

---

What is claimed is:

1. An isolated bacterial nucleic acid molecule encoding a bacterial protein having a molecular weight of approximately 46 kDa as determined by SDS-PAGE and comprising the amino acid sequence set forth in SEQ ID NO:3.

2. The nucleic acid molecule of claim 1 wherein the bacterial protein is of a Haemophilus strain.

3. The nucleic acid molecule of claim 2 wherein the bacterial strain is an *H. influenzae* strain.

4. A vector for transformation of a host comprising the nucleic acid molecule of claim 1.

5. The vector of claim 4 wherein the nucleic acid molecule is operatively coupled to expression means for expression by the host of the bacterial protein.

6. A host cell comprising the vector of claim 4.

7. A host cell comprising the vector of claim 5.

8. A method of producing a bacterial protein, having a molecular weight of approximately 46 kDa as determined by SDS-PAGE and comprising the amino acid sequence set forth in SEQ ID NO:3, comprising:
culturing the host cell of claim 6 under conditions that allow expression of said protein; and
recovering said protein.

9. A method of producing a bacterial protein, having a molecular weight of approximately 46 kDa as determined by SDS-PAGE and comprising the amino acid sequence set forth in SEQ ID NO:3, comprising:
culturing the host cell of claim 7 under conditions that allow expression of said protein; and
recovering said protein.

\* \* \* \* \*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1011 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
ATGAAAAAAC TTTTAAAAAT TAGTGCCATT TCTGCCGCAC TTTTAAGTGC GCCAATGATG      60
GCGAATGCCG ATGTATTAGC ATCAGTAAAA CCTTTAGGCT TTATTGTTTC ATCTATTGCA     120
GATGGCGTAA CTGGTACACA AGTCCTTGTT CCTGCTGGCG CCTCTCCGCA TGATTACAAT     180
```

-continued

```
TTGAAATTAT CTGATATTCA AAAAGTAAAA TCTGCAGATT TAGTTGTATG GATTGGTGAA      240

GACATTGATT CATTCTTAGA CAAACCAATT AGCCAAATTG AACGTAAAAA AGTGATTACC      300

ATTGCCGATC TTGCGGATGT AAAACCTTTA TTAAGTAAAG CTCACCATGA GCATTTCCAT      360

GAAGATGGCG ATCATGATCA TGACCATAAG CACGAACACA AACATGATCA TAAACACGAC      420

CATGACCATG ATCATGATCA TAAACACGAG CATAAACACG ACCACGAACA TCATGATCAT      480

GATCATCACG AGGGTTTAAC AACAAACTGG CACGTTTGGT ATTCTCCAGC TATCAGCAAA      540

ATTGTTGCAC AAAAAGTAGC GGATAAATTA ACTGCACAAT TCCCAGATAA AAAAGCGTTA      600

ATTGCACAAA ATCTTTCAGA TTTTAACCGC ACTTTGGCAG AACAAAGTGA AAAAATTACG      660

GCACAACTTG CAAATGTTAA AGATAAAGGT TTCTACGTTT TCCACGATGC TTATGGTTAT      720

TTCAACGATG CTTATGGTTT AAAACAAACG GGTTACTTTA CCATCAATCC ATTAGTGGCA      780

CCGGGTGCAA AAACTTTAGC GCACATTAAA GAAGAAATTG ATGAACATAA AGTAAATTGC      840

TTATTCGCAG AGCCTCAATT TACGCCAAAA GTGATTGAGT CTTTAGCGAA AAATACTAAA      900

GTCAATGTAG ACAACTCGA CCCAATTGGC GATAAAGTTA CTTTAGGTAA AAATTCTTAT      960

GCAACATTCT TGCAATCTAC TGCAGATAGC TACATGGAAT GTTTAGCTAA A             1011
```

(2) INFORMATION FOR SEQ ID NO:2:

(i) SEQUENCE CHARACTERISTICS:
        (A) LENGTH: 337 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Lys Lys Leu Leu Lys Ile Ser Ala Ile Ser Ala Ala Leu Leu Ser
 1               5                  10                  15

Ala Pro Met Met Ala Asn Ala Asp Val Leu Ala Ser Val Lys Pro Leu
                20                  25                  30

Gly Phe Ile Val Ser Ser Ile Ala Asp Gly Val Thr Gly Thr Gln Val
            35                  40                  45

Leu Val Pro Ala Gly Ala Ser Pro His Asp Tyr Asn Leu Lys Leu Ser
        50                  55                  60

Asp Ile Gln Lys Val Lys Ser Ala Asp Leu Val Val Trp Ile Gly Glu
65                  70                  75                  80

Asp Ile Asp Ser Phe Leu Asp Lys Pro Ile Ser Gln Ile Glu Arg Lys
                85                  90                  95

Lys Val Ile Thr Ile Ala Asp Leu Ala Asp Val Lys Pro Leu Leu Ser
                100                 105                 110

Lys Ala His His Glu His Phe His Glu Asp Gly Asp His Asp His Asp
            115                 120                 125

His Lys His Glu His Lys His Asp His Lys His Asp His Asp His Asp
        130                 135                 140

His Asp His Lys His Glu His Lys His Asp His Glu His His Asp His
145                 150                 155                 160

Asp His His Glu Gly Leu Thr Thr Asn Trp His Val Trp Tyr Ser Pro
                165                 170                 175

Ala Ile Ser Lys Ile Val Ala Gln Lys Val Ala Asp Lys Leu Thr Ala
                180                 185                 190

Gln Phe Pro Asp Lys Lys Ala Leu Ile Ala Gln Asn Leu Ser Asp Phe
```

```
            195                 200                 205
Asn Arg Thr Leu Ala Glu Gln Ser Glu Lys Ile Thr Ala Gln Leu Ala
        210                 215                 220

Asn Val Lys Asp Lys Gly Phe Tyr Val Phe His Asp Ala Tyr Gly Tyr
225                 230                 235                 240

Phe Asn Asp Ala Tyr Gly Leu Lys Gln Thr Gly Tyr Phe Thr Ile Asn
                245                 250                 255

Pro Leu Val Ala Pro Gly Ala Lys Thr Leu Ala His Ile Lys Glu Glu
                260                 265                 270

Ile Asp Glu His Lys Val Asn Cys Leu Phe Ala Glu Pro Gln Phe Thr
            275                 280                 285

Pro Lys Val Ile Glu Ser Leu Ala Lys Asn Thr Lys Val Asn Val Gly
        290                 295                 300

Gln Leu Asp Pro Ile Gly Asp Lys Val Thr Leu Gly Lys Asn Ser Tyr
305                 310                 315                 320

Ala Thr Phe Leu Gln Ser Thr Ala Asp Ser Tyr Met Glu Cys Leu Ala
                325                 330                 335

Lys
```

(2) INFORMATION FOR SEQ ID NO:3:

(i) SEQUENCE CHARACTERISTICS:
        (A) LENGTH: 313 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Val Leu Ala Ser Val Lys Pro Leu Gly Phe Ile Val Ser Ser Ile Ala
1               5                   10                  15

Asp Gly Val Thr Gly Thr Gln Val Leu Val Pro Ala Gly Ala Ser Pro
                20                  25                  30

His Asp Tyr Asn Leu Lys Leu Ser Asp Ile Gln Lys Val Lys Ser Ala
            35                  40                  45

Asp Leu Val Val Trp Ile Gly Glu Asp Ile Asp Ser Phe Leu Asp Lys
50                  55                  60

Pro Ile Ser Gln Ile Glu Arg Lys Lys Val Ile Thr Ile Ala Asp Leu
65                  70                  75                  80

Ala Asp Val Lys Pro Leu Leu Ser Lys Ala His His Glu His Phe His
                85                  90                  95

Glu Asp Gly Asp His Asp His Asp His Lys His Glu His Lys His Asp
                100                 105                 110

His Lys His Asp His Asp His Asp His Asp His Lys His Glu His Lys
            115                 120                 125

His Asp His Glu His His Asp His Asp His His Glu Gly Leu Thr Thr
        130                 135                 140

Asn Trp His Val Trp Tyr Ser Pro Ala Ile Ser Lys Ile Val Ala Gln
145                 150                 155                 160

Lys Val Ala Asp Lys Leu Thr Ala Gln Phe Pro Asp Lys Lys Ala Leu
                165                 170                 175

Ile Ala Gln Asn Leu Ser Asp Phe Asn Arg Thr Leu Ala Glu Gln Ser
            180                 185                 190

Glu Lys Ile Thr Ala Gln Leu Ala Asn Val Lys Asp Lys Gly Phe Tyr
        195                 200                 205
```

```
Val Phe His Asp Ala Tyr Gly Tyr Phe Asn Asp Ala Tyr Gly Leu Lys
    210                 215                 220

Gln Thr Gly Tyr Phe Thr Ile Asn Pro Leu Val Ala Pro Gly Ala Lys
225                 230                 235                 240

Thr Leu Ala His Ile Lys Glu Glu Ile Asp Glu His Lys Val Asn Cys
                245                 250                 255

Leu Phe Ala Glu Pro Gln Phe Thr Pro Lys Val Ile Glu Ser Leu Ala
                260                 265                 270

Lys Asn Thr Lys Val Asn Val Gly Gln Leu Asp Pro Ile Gly Asp Lys
            275                 280                 285

Val Thr Leu Gly Lys Asn Ser Tyr Ala Thr Phe Leu Gln Ser Thr Ala
    290                 295                 300

Asp Ser Tyr Met Glu Cys Leu Ala Lys
305                 310
```

(2) INFORMATION FOR SEQ ID NO:4:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Val Leu Ala Ser Val Lys Pro Leu Gly Phe Ile Val Ser Ser Ile Ala
1               5                   10                  15

Asp Gly Val Thr Gly Thr Gln Val Leu Val Pro Ala Gly Ala Ser Pro
            20                  25                  30

His Asp Tyr
        35
```